United States Patent [19]

Mueller

[11] 4,069,244

[45] Jan. 17, 1978

[54] FLUORINATED AMPHOTERIC AND CATIONIC SURFACTANTS

[75] Inventor: Karl Friedrich Mueller, New York, N.Y.

[73] Assignee: Ciba-Geigy Corporation, Ardsley, N.Y.

[21] Appl. No.: 538,432

[22] Filed: Jan. 3, 1975

[51] Int. Cl.$^2$ .................. C07C 101/04; C07D 207/08; C11D 1/00; B01F 17/28
[52] U.S. Cl. ........................... 260/501.12; 260/534 S; 260/250 A; 260/251 R; 260/268 R; 260/268 C; 260/283 S; 260/293.85; 260/294.8 G; 260/307 FA; 260/326.12 R; 260/326.43; 260/326.5 FM; 260/294.8 C; 544/161; 548/300; 252/2; 252/89 R; 252/353; 252/354; 252/355; 252/356; 252/357
[58] Field of Search ............ 260/501.12, 513 F, 534 S

[56] References Cited

U.S. PATENT DOCUMENTS 3,471,518 10/1969 Hager .................................. 260/345.9
3,839,425 10/1974 Barlett ............................. 260/501.12

*Primary Examiner*—Nicky Chan
*Attorney, Agent, or Firm*—Nestor W. Shust

[57] ABSTRACT

The invention is directed to fluorinated compounds of the formula

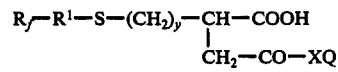

wherein $R_f$ is a perfluoroalkyl or perfluoroalkoxy-perfluoroalkyl group, $R^1$ is a branched or straight chain alkylene, alkylenethioalkylene, alkyleneoxyalkylene or alkyleneiminoalkylene group, X is oxygen or an amino group, Q is an organic group containing at least one amino group and $y$ is zero or 1, and the corresponding succinimides. These compounds are useful as surfactants.

13 Claims, No Drawings

FLUORINATED AMPHOTERIC AND CATIONIC SURFACTANTS

BACKGROUND OF THE DISCLOSURE

The below described invention deals with novel perfluoroalkyl group containing surfactants. The importance of the surfactants resides in the fact that they act as wetting, emulsifying, solubilizing and/or dispersing agents. Although surfactants have been prepared from many classes of compounds, more recently surfactants containing perfluoro alkyl ($R_f$) groups have been reported. $R_f$-substituted surfactants are especially valuable because they are known to reduce the surface tension of liquids more than any other surfactant. For instance, in water, surface tension of less than 17 dynes/cm can be obtained with fluorinated surfactants, whereas the non-fluorinated hydrocarbon analogs reduce the surface tension of water only to about 30 dynes/cm. For this reason the fluorinated surfactants have found applications in such diverse areas as emulsion-polymerizations, self-polishing floor waxes, electroplating, corrosion inhibitors, paints, and fire fighting compositions.

A variety of fluorinated, amphoteric and cationic surfactants have been disclosed in U.S. Pat. Nos. 2,764,602, 3,555,089 and 3,681,413 and in German Offenlegungschrift 2,120,868; 2,127,232; 2,165,057 and 2,315,326. Although the compounds of the present invention also contain $R_f$ groups, they are substantially different from the surfactants disclosed in the above listed patents.

Possible intermediates which can be used in preparing the surfactants of this invention are disclosed in U.S. Pat. No. 3,471,518 wherein the addition of $R_f$-alkylenethiols to maleic acid and maleates is disclosed and U.S. Pat. No. 3,706,787 wherein the addition products of $R_f$-thiols are dialkyl maleates and monoalkyl maleates are disclosed. German Offenlegungschrift No. 2,219,642 discloses $R_f$-alkylenethiol addition products with dialkyl amino-alkyl acrylates and methacrylates, which compounds are cationic surfactants and do not possess a 1,2-dicarboxylic moiety. While all fluorinated amphoteric surfactants of the prior art are synthesized by quaternization of an appropriate tertiary amine with an alkylating agent, such as lactones, sultones or halogenated acids, the amphoteric surfactants of this invention are prepared by a simple ring-opening reaction without the use of potentially carcinogenic alkylating agents. The surfactants of this invention are superior wetting agents, especially when used in combination with other fluorinated and nonfluorinated surfactants. Furthermore, they can be manufactured much more economically and safely.

DETAILED DISCLOSURE

The present invention is directed to novel amphoteric and cationic $R_f$-surfactants. These compounds can be represented by the formulae

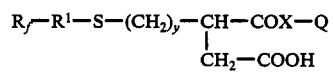

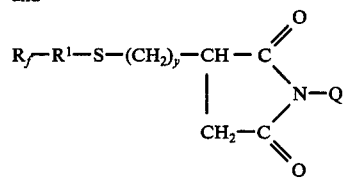

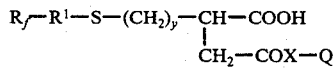

and its isomer wherein $R_f$ is straight or branched chain perfluoroalkyl of 1 to 18 carbon atoms of said perfluoroalkyl substituted by perfluoroalkoxy of 2 to 6 carbon atoms, $R^1$ is branched or straight chain alkylene of 1 to 12 carbon atoms, alkylenethioalkylene of 2 to 12 carbon atoms, alkyleneoxyalkylene of 2 to 12 carbon atoms or alkyleneiminoalkylene of 2 to 12 carbon atoms where the nitrogen atom contains as a third substituent, hydrogen or alkyl of 1 to 6 carbon atoms, $y$ is 1 or zero, X is oxygen or —NR, wherein R is hydrogen, lower alkyl of 1 to 6 carbon atoms, hydroxyalkyl of 1 to 6 carbon atoms, or X together with Q forms a piperazine ring, and Q is a nitrogen containing group selected from 1. an aliphatic amino group selected from

wherein $R^2$ is a linear or branched alkylene of 2 to 12 carbon atoms, oxygen or sulfur interrupted linear or branched alkylene of up to 60 carbon atoms, or hydroxyl substituted alkylene. Preferably $R^2$ is a straight chain or branched alkylene of 2 to 5 carbon atoms;

$k$ is 1 or zero, with the proviso, that if X is oxygen, $k$ is 1;

$R^3$ and $R^4$ are independently of each other hydrogen, alkyl group, substituted alkyl group of 1 to 20 carbon atoms; phenyl group, an alkyl or halogen substituted phenyl group of 6 to 20 carbon atoms, polyethoxy or polypropoxy group of 2 to 20 alkoxy units with the proviso that if X is oxygen, $R^3$ and $R^4$ are not hydrogen. The alkyl substituents can be alkyl of 1 to 5 carbons, dienyl, hydroxyl, carboxyl, halogen, alkylene dialkylphosphonate such as methylene-diethylphosphonate or a group

Phenyl substituents can be methyl, halogen or hydroxyl. Preferably $R^3$ and $R^4$ are alkyl groups of 1 to 4 carbons.

$A^-$ is any anion which forms an ammonium salt of the formula $NH_4 + A-$.

Anion $A^-$ is derived from alkyl halides, benzene or chlorobenzene sulfonate esters of alkyl alcohols and methyl and ethyl sulfates. $A^-$ is preferably $Cl^-$, $Br^-$, $CH_3CH_2OSO_3^-$ or $CH_3OSO_3^-$.

$R^5$ is hydrogen, an alkyl group or hydroxyalkyl group, aralkyl or groups of the formula $-(CH_2)_n-COO$-alkyl, said alkyl group having 1 to 18 carbons. Preferably, $R^5$ is methyl, ethyl, propyl, butyl or benzyl.

$G^-$ is a group selected from the groups $-(CH_2)_n-COO^\ominus$;       $-(CH_2)_3SO_3^\ominus$;
$-CH-COO^\ominus$   and   $-C-COO^\ominus$
  |                           ||
  $CH_2-COOH$                 $CH-COOH$ where $n$ is 1 to 5;

2. cyclic amino groups selected from

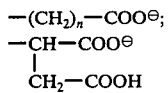 (2a)

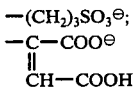 (2b)

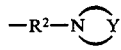 (2c)

wherein
Y is a diradical group of the formulae:

$-(CH_2)_4-$ $-(CH_2)_5-$
$-(CH_2)_2-O-(CH_2)_2-$

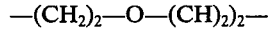, wherein
$R^2$, $R^5$, $A^-$ and $G^-$ are as defined above,
$R^7$ and $R^8$ are independent hydrogen, a lower alkyl or hydroxy-lower alkyl group of 1 to 6 carbon atoms, with the proviso, that if X is oxygen, $R^8$ cannot be hydrogen.

3. aromatic amino groups selected from

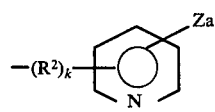 (3a)

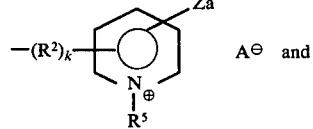 (3b)

-continued

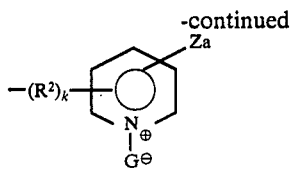 (3c)

4. fused-ring aromatic amino group selected from

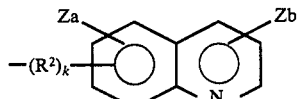 (4a)

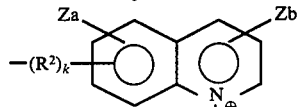 (4b)

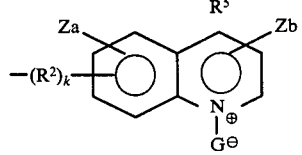 (4c)

wherein
Z is halogen or methyl,
$a + b$ is an integer from 0–3; and 5. a heterocyclic amino group of the formula $-(R^2)_k-E$ (5a)

$-(R^2)_k-E^+-R^5 A^-$ (5b)

$-(R^2)_k-E^+-G^-$ (5c)

where
k is one or zero and
E is selected from N-hydroxyalkyl or N-aminoalkyl, substituted pyrrole, pyrazole, imidazole, triazole, indole or indazole, hydroxyalkyl and aminoalkyl ring-substituted pyridazine, pyrimidino, pyrazino or quinoxalino.

The compounds represented above by formulae I and II where Q is of structures (1a), (2a), (3a), (4a) or (5a) exist in solution in the form of their inner salts, having the general structures

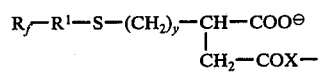 Ia

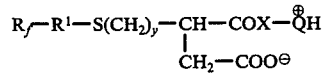 IIa and thus are amphoteric surfactants.

The compounds of structure III are obtained through imidization of compounds of structures I and II, when X is —NH— by heating, either in bulk or in solution, to a temperature of about 100° C. The compounds of this invention where Q is of structures (1a), (2a), (3a), (4a) or (5a) are prepared from maleic or itaconic anhydrides, perfluoroalkyl group-containing thiols and a polyamine or an aminoalcohol. Typically, they are prepared in two steps: first, maleic anhydride or itaconic anhydride is reacted with an equimolar amount of either an alcohol containing at least one tertiary amino group, or a primary or secondary amine containing at least one more primary, secondary or tertiary amino group, to form an unsaturated intermediate half ester or half amide of structures:

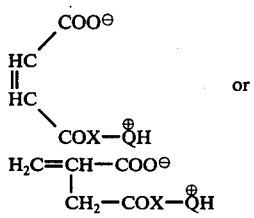

where X is defined as above and Q is of structures (1a), (2a), (3a), (4a) or (5a).

Compounds of this structure are described in the literature as comonomers of vinyl polymerization.

For instance,

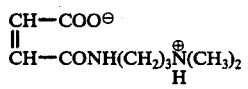

N-(3-dimethylaminopropyl)maleic acid amide, in U.S. Pat. No. 2,821,521.

For compounds in which X is

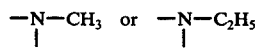

and Q is $-CH_2CH_2-N(CH_3)_2$ the intermediate undergoes cyclization and forms a compound of structure:

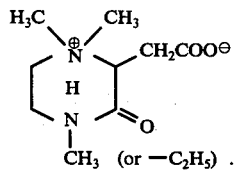

These compounds are new and their structures have been confirmed by NMR and by the absence of an acidic hydrogen.

Instead of preparing the intermediate from the anhydride by ring opening, other synthesis routes can be used; as for instance, transesterification or transamidification of a lower alkyl maleic, fumaric or itaconic half ester.

Synthesis of the novel surfactants is completed in a second reaction step during which the perfluoroalkyl substituted thiol is added to the double bond of the intermediate by base catalysis. This reaction normally proceeds at room temperature, except where an intermediate of the above described cyclic type is formed; in this case addition of the thiol occurs only at temperatures of 85° C and above.

Alternately, the synthetic route can be reversed and the $R_f$-thiol added to the unsaturated, cyclic anhydride or its lower alkyl monoester through base-catalysis or by a free-radical mechanism. The intermediate is then reacted with an alcohol containing at least one tertiary amino group or a primary or secondary amine containing at least one more primary, secondary or tertiary amino group which yields the desired product. The first synthesis route is preferred because of the high yield and purity of the product.

The mono-esters can be easily synthesized by reacting an equimolar amount of an unsaturated cyclic anhydride and the amino alcohol, either in bulk or in solution. The mono-amides can be prepared by reacting at a temperature below 50° C in a solvent equimolar amounts of an unsaturated cyclic anhydride with a polyamine. The useful solvents are such as methylethyl ketone, diethylene glycol dimethylether, dimethylformamide, tetrahydrofuran, perchloroethylene, 1,1,1-trichloroethane, dichloromethane, dioxane, dimethylsulfoxide, N-methyl pyrrolidone. The amides can also be prepared in water or a mixture of water and an above listed solvent by adding the anhydride to the aqueous solution of the amine as described in greater detail in Canadian Pat. No. 828,195.

The $R_f$-substituted thiol addition to the mono-esters and mono-amides is carried out in solution or in bulk at a temperature between 20° to 100° C. Useful solvents are alcohols such as methanol, ethanol, n-propanol, isopropanol, n- and isobutanol, amyl alcohol, n-hexanol, cyclohexane, benzyl alcohol and the like; ethers such as dimethyl ether, methyl ethyl ether, diethyl ether, di-n-propyl ether, diisopropyl ether, methyl n-butyl ether, ethyl n-butyl ether, ethylene glycol dimethyl ether, divinyl ether, diallyl ether, tetrahydrofuran and the like; ketones such as acetone, methyl ethyl ketone, methyl n-propyl ketone, diethyl ketone, hexanone-2, hexanone-3, methyl t-butyl ketone, di-n-propyl ketone, diisopropyl ketone, diisobutyl ketone, chloroacetone, diacetyl, acetyl acetone, mesityl oxide, cyclohexanone and the like; N-methyl pyrrolidone, dimethylformamide, acetonitrile, benzene, chlorobenzene, chloroform, methylenechloride, trichloromethane, carbontetrachloride, dioxane, nitrobenzene, toluene and the like. Water can also be employed or a mixture of water and any one of the preceeding solvents.

Preferred are solvent mixtures containing methanol, ethanol, isopropanol, carbitol or butylcarbitol, or water. If for a subsequent reaction, for instance quaternization with propanesultone, the alcohol has to be removed, a mixture of N-methylpyrrolidone and a low boiling alcohol such as methanol is preferred. Since the malic mono-esters or maleic mono-amides already contain an amino group, no additional amine has to be added to catalyze the thiol addition.

The novel surfactants thus obtained are directly soluble in water or water/co-solvent mixtures. The solutions are essentially neutral. In dilute aqueous solution the tert-aminoalkyl mono-esters and mono-amides form polymeric aggregates leading to very high viscosities; these gel-type solutions are easily broken up by addition of a co-solvent, such as butycarbitol, or a nonionic co-surfactant, such as an ethoxylated alkyl-phenol.

The compounds of this invention where Q is of structures (1b and c), (2b and c), (3b and c), (4b and c) and (5b and c) are prepared by quaternization of the amphoteric surfactants prepared as described above.

The quaternization reaction can be carried out in the presence or absence of an inert solvent. Suitable solvents are diethyl ether, acetonitrile, dimethylformamide, N-methylpyrrolidone and the like.

The temperature of the reaction is not critical and may range from 0° to about 150° C depending on the reactivity of the quaternizing agent.

The resultant quaternary ammonium compounds are frequently obtained as solids when an inert solvent is employed. They can be readily separated, washed and dried. The products can be isolated from solution by addition of a nonsolvent, as will be known to one skilled in the art. The products can be further purified if desired by recrystallization from an appropriate solvent or solvent mixture. Products obtained as viscous liquids can be further purified by extraction with a suitable solvent.

If the amino alcohol is a diol or a polyamine which contains at least three amino groups at least two of which are primary or secondary amino groups, it can be reacted with two moles of maleic or itaconic anhydride and two moles of $R_f$-alkylenethiol yielding bis-$R_f$-alkylenethiosuccinic acid half-amides, half-esters and succinimides which can be represented by the formulae $$\left[ \begin{array}{c} R_f-R^1-S-(CH_2)_y-CH-COOH \\ | \\ CH_2COX \end{array} \right]_2 T$$

and its isomer or $$\left[ R_f-R^1-S-(CH_2)_y-\overset{H}{\underset{|}{C}}-\overset{\overset{O}{\|}}{C}\underset{\underset{O}{\|}}{\overset{}{\underset{C}{N}}}\right]_2 T$$

wherein T is a nitrogen containing divalent group selected from $$-R^2-N\overset{R^3}{\underset{(R^2)-}{\diagdown}} \qquad (1)$$

$$-R^2-N\underset{}{\diagdown}\overset{H}{\underset{}{\bigcirc}}N-R^2- \qquad (2)$$

$$-R^9-\underset{|}{\overset{}{\bigcirc}}N \qquad (3)$$

where $R^9$ is an aliphatic hydro-carbon triradical of 3 to 10 carbon atoms, preferably of 3 to 5 carbons. An example of structure (3) is the 3-pyridylpentane-1,5-diradical.

If the structures I and II X is oxygen, Q is derived from tert-amino group containing alcohols of the formula $$HO-R^2-N\overset{R^3}{\underset{R^4}{\diagdown}} \qquad (1)$$

where $R^3$ and $R^4$ are as defined above.

Illustrative examples of the above represented alcohols are

HO—CH$_2$—CH$_2$—N(CH$_3$)$_2$

HO—CH$_2$—CH$_2$—N(C$_2$H$_5$)$_2$

HO—(CH$_2$)$_3$—N(CH$_3$)$_2$

HO—(CH$_2$)$_3$—N(C$_2$H$_5$)$_2$

HO—(CH$_2$)$_3$—N(C$_3$H$_7$)$_2$

HO—(CH$_2$)$_4$—N(CH$_3$)$_2$

HO—(CH$_2$)$_5$—N(CH$_3$)$_2$

HO—(CH$_2$)$_6$—N(CH$_3$)$_2$

HO(CH$_2$)$_8$—N(CH$_3$)$_2$

HO(CH$_2$)$_{10}$—N(CH$_3$)$_2$

HO(CH$_2$)$_{12}$—N(CH$_3$)$_2$

HO—CH—CH$_2$N(CH$_3$)$_2$
       |
       CH$_3$

HO—(CH$_2$CH$_2$O)$_x$CH$_2$CH$_2$—N—(CH$_2$) CH$_3$
(CH$_2$CH$_2$O)$_y$H where $x + y = 3-25$ and $z = 1-20$ HO—CH$_2$CH$_2$—N(phenyl)CH$_2$CH$_2$OH HO—CH$_2$CH$_2$—N(toloyl)CH$_2$CH$_2$OH HO—CH—CH$_2$—N(phenyl)CH$_2$CH—OH
    |                              |
    CH$_3$                         CH$_3$ $$HOCH_2CH_2-N-CH_2CH_2OH \atop CH_2-P=O \overset{OC_2H_5}{\underset{OC_2H_5}{}}$$

Another class of tert-amino containing alcohols are cyclic compounds of the formula $$HO-R^2-N\!\!\frown\!\!Y \qquad (2)$$

where
$R^2$ and Y are as defined above.

Illustrative examples of the above represented alcohols are

HO(CH$_2$)$_2$—N⟨ H ⟩

HO(CH$_2$)$_2$—N⟨ H ⟩

HO(CH$_2$)$_2$—N⟨ H O ⟩

HO(CH$_2$)$_3$—N⟨ H ⟩N—(CH$_2$)$_3$OH
                 |
                 CH$_3$

Still other classes of tert-amino group containing alcohols are of the formulae

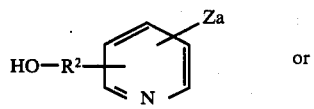 (3)

or

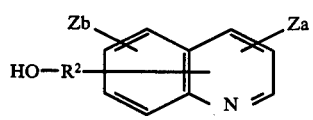 (4)

or

HO(R²)<sub>k</sub>—E   (5)

wherein R², Z, E, a, b and k are as defined above.

Illustrative examples of such alcohols are
2-, 3-, and 4-, (2'-hydroxyethyl)pyridine
3-methyl-4-(2'-hydroxyethyl)pyridine
2-methyl-4-(2'-hydroxyethyl)pyridine
2-, 3-, 4-, 5-, 6-, 7-, and 8-(2'-hydroxyethyl)quinolines
3-pyridyl-1,5-pentane diol.

When in formulae I or II X is —NR, such a moiety can be derived from a primary or secondary amine containing at least one other amino group. Such amines can be represented by the formula

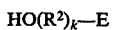 (1)

where
R to R⁴ and k are as defined above.

Illustrative examples of the above represented amines are $NH_2(CH_2)_2N(CH_3)_2$ $NH_2(CH_2)_2N(C_4H_9)_2$ $CH_3NH(CH_2)_2N(CH_3)_2$ $NH_2(CH_2)_3N(C_3H_7)_2$ $NH_2(CH_2)_4N(C_2H_5)_2$ $NH_2(CH_2)_5N(C_2H_3)_2$ $NH_2(CH_2)_8N(C_3H_7)_2$ $NH_2(CH_2)_2N(C_2H_5)_2$ $NH_2(CH_2)_3N(CH_3)_2$ $CH_3NH(CH_2)_2N(C_2H_3)_2$ $NH_2(CH_2)_3N(C_4H_9)_2$ $CH_3NH(CH_2)_4N(CH_3)_2$ $NH_2(CH_2)_6N(C_2H_5)_2$ $NH_2(CH_2)_8N(C_4H_9)_2$ $NH_2(CH_2)_2N(C_3H_7)_2$ $NH_3(CH_2)_3N(C_2H_5)_2$ $C_2H_5NH(CH_2)_2N(C_2H_5)_2$ $NH_2(CH_2)_4N(CH_3)_2$ $NH_2(CH_2)_5N(CH_3)_2$ $NH_2(CH_2)_6N(C_3H_7)_2$ $NH_2(CH_2)_{10}N(C_3H_7)_2$ $NH_2(CH_2)_{12}N(C_3H_7)_2$ $CH_3NH(CH_2)_3N(CH_3)_2$ $H_2N(CH_2)_2N(CH_2CH_2OH)_2$ $H_2N—N(CH_3)_2$ $CH_3NH—N(CH_3)_2$ $H_2NCH_2CH_2CH_2NHCH_3$ $H_2NCH_2CH_2NHCH_3$ $H_2NCH_2CH_2CH_2NH_2$ $H_2NCH_2CH_2NH_2$ $H_2NCH_2CH_2CH_2N(CH_3)CH_2CH_2CH_2NH_2$ $H_2NCH_2CH_2NHCH_2CH_2OH$.

Another class of primary and secondary amines containing at least one other amino group are heterocyclic compounds of the formulae

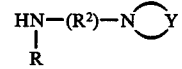 (2)

or

wherein
R, R², R⁵ and Y are as defined above.

Illustrative examples of the amines above are
N-(2'-aminoethyl)piperidine
N-(2'-aminoethyl)morpholine
N-(4'-aminobutyl)piperidine
N-(2'-aminoethyl)-pyrrolidine
N-methyl piperazine
piperazine
N-(2-hydroxyethyl)piperazine.

Still other classes of primary and secondary amines containing at least one other amino group are aromatic heterocyclic compounds containing five and six membered rings. These classes include

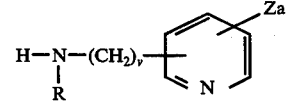 (3)

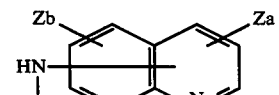 (4)

and $$H_2N(R^2)_k\text{—}E \quad (5)$$

wherein
R, $R^2$, Z, E, a and b are as defined above, and
v is an integer of from 0 to 12.

Illustrative examples of the amines represented above are
- 2-aminomethylpyridine
- 2-(2'-aminoethyl)pyridine
- 3-(2'-aminoethyl)pyridine
- 3-aminomethylpyridine
- 2,6-dichloro-3-aminomethylpyridine
- 2-methyl-3-(2'-aminoethyl)pyridine
- 3-(4'-aminobutyl)pyridine
- 4-aminomethylpyridine
- 4-(2'-aminoethyl)pyridine
- 2-aminopyridine
- 3, 4, 5 or 6-methyl-2-aminopyridine
- 3, 4, 5 or 6-chloro-2-aminopyridines
- 3-aminopyridine
- 2-chloro-6-methyl-3-aminopyridine
- 4-aminopyridine
- dichloro-4-aminopyridines
- 2-aminopyrimidine
- 2-, 3-, 4-, 5-, 6-, 7- and 8-(4'-aminobutyl)quinolines
- 2-, 3-, 4-, 5-, 6-, 7- and 8-(3'-methylaminopropyl)-quinolines
- 2, 3, 4, 5, 6, 7 or 8-aminoquinolines
- chloroaminoquinolines
- methylaminoquinolines
- quanine
- adenine.

Compounds having structures I, II or III, where Q is of structure (1b), (2b), (3b) or (4b) are derived from the corresponding amines by quaternization with compounds of the structures $$R^5A$$

where $R^5$ and A are as defined above.

Suitable compounds of the formula $R^5A$ are those in which $R^5$ is an alkyl group of 1 to 18 carbon atoms and A is any anion which forms an ammonium salt of the formula $NH_4^+A^-$ having a solubility in water of at least about 1%. Useful examples of $R^5A$ are the methyl-, ethyl-, propyl-, isopropyl-, butyl-, isobutyl-, sec-butyl-, hexyl-, octyl-, ethylhexyl-, decyl-, dodecyl-, tetradecyl-, hexadecyl-, octadecyl-chlorides, bromides and iodides; benzylchloride; halo-alkanoic acid esters, and halo alkyl-alkyl ethers.

The normal alkyl halides, i.e., n-propyl, n-butyl, n-octyl or n-hexadecyl, are preferred. Also useful are the toluene, benzene and chlorobenzene sulfonate esters of methyl, ethyl, propyl, butyl and like alcohols, and methyl and ethyl sulfate. When methyl or ethyl sulfate ($R_2SO_4$) is used, the anion A in the product of the present invention will usually be a mixture of $RSO_4^-$ and

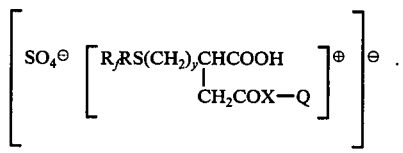

Also useful are mineral acids, such as HCl, HBr, HI, $H_3PO_4$ and $H_2SO_4$, and organic acids, such as acetic, formic, acrylic acids.

The compounds of structures I, II and III where Q is of structure (1c), (2c), (3c), (4c) or (5c) are similarly derived from the corresponding amines by quaternization $$\text{Hal—}R^6\text{—COOH} \quad (a)$$

wherein
Hal stands for chlorine, bromine or iodine,
$R^6$ is an alkylene group of 1 to 5 carbon atoms, or a group

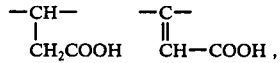

(b) 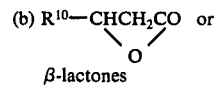
β-lactones (c) 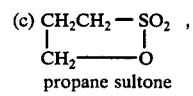
propane sultone wherein $R^{10}$ is hydrogen or an alkyl group of 1 to 6 carbon atoms.

The perfluoroalkyl thiols employed in the preparation of the compounds of this invention are well known in the prior art. For example, thiols of the formula $R_fR^1$—SH have been described in a number of U.S. patents including U.S. Pat. Nos. 2,894,991; 2,961,470; 2,965,677; 3,088,849; 3,172,190; 3,544,663 and 3,655,732.

Thus U.S. Pat. No. 3,655,732 discloses mercaptans of formula $$R_f\text{—}R^1\text{—SH}$$

where
$R^1$ is alkylene of 1 to 16 carbon atoms and $R_f$ is perfluoroalkyl and teaches that halides of formula $R_f$—$R^1$—hal are well known; reaction of $R_fI$ with ethylene under free-radical conditions gives $R_f(CH_2CH_2)_aI$ while reaction of $R_fCH_2I$ with ethylene gives $R_fCH_2(CH_2CH_2)_aI$ as is further taught in U.S. Pat. Nos. 3,088,849; 3,145,222; 2,965,659 and 2,972,638.

U.S. Pat. No. 3,655,732 further discloses compounds of formula $$R_f\text{—}R'\text{—}X\text{—}R''\text{—SH}$$

where
R' and R" are alkylene of 1 to 16 carbon atoms, with the sum of the carbon atoms of R' and R" being no greater than 25; $R_f$ is perfluoroalkyl of 4 through 14 carbon atoms and X is —S— or —NR'''— where R''' is hydrogen or alkyl of 1 through 4 carbon atoms.

U.S. Pat. No. 3,544,663 teaches that the mercaptan $$R_fCH_2CH_2SH$$

where
$R_f$ is perfluoroalkyl of 5 to 13 carbon atoms, can be prepared by reacting the perfluoroalkyl alkylene iodide with thiourea or by adding $H_2S$ to a perfluoroalkyl substituted ethylene ($R_4$—CH=$CH_2$), which in turn can be prepared by dehydrohalogenation of the halide $R_fCH_2CH_2$—hal.

The reaction of the iodide $R_f$—$R^1$—I with thiourea followed by hydrolysis to obtain the mercaptan $R_f$—$R^1$—SH is the preferred synthetic route. The reaction is applicable to both linear and branched chain iodides. Many useful perfluoroalkoxyalkyl iodides are described in Australian Application No. 36868 filed Apr. 24, 1968, of general formula $$(CF_3)_2CFO\ CF_2CF_2(CH_2CH_2)_mI$$

where
m is 1–3.
Particularly preferred herein are the thiols of formula $$R_fCH_2CH_2SH$$

where
$R_f$ is perfluoroalkyl of 6 to 12 carbon atoms. These $R_f$-thiols can be prepared from $R_fCH_2CH_2I$ and thiourea in very high yield.

Illustrative examples of preferred perfluoroalkylalkylenethiols are $$C_4F_9CH_2CH_2SH$$

$$C_6F_{13}CH_2CH_2SH$$

$$C_8F_{17}CH_2CH_2SH$$

$$C_{10}F_{21}CH_2CH_2SH$$

$$C_{12}F_{25}CH_2CH_2SH$$

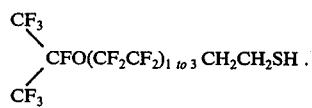

Especially preferred perfluoroalkylalkylenethiols are $$C_6F_{13}CH_2CH_2SH$$

$$C_8F_{17}CH_2CH_2SH$$

$$C_{10}F_{21}CH_2CH_2SH$$

and mixtures thereof.

Unsaturated dicarboxylic cyclic anhydrides which can be employed in preparing the surfactants of this invention can be maleic and alkyl and halogen substituted maleic anhydrides such as citraconic and chloro and dichloromaleic anhydrides. Preferred are itaconic and maleic and most preferred maleic anhydride.

The compounds of this invention, as noted above, are effective surfactants and therefore can be employed in all applications where surfactants are required. These surfactants would be employed as prior art surfactants which is self evident to those skilled in the art. Specific examples where the instant surfactant can be employed are as wetting agents in coatings, waxes, emulsions, paints. They are especially useful when formulated with other non-fluorinated surfactants as fire fighting agents. A particular advantage of these surfactants is their low toxicity to aquatic life.

A particular advantage of the compounds of this invention where Q is represented by structures (1a), (2a), (3a), (4a) and (5a) is that they are amphoteric surfactants made without a specific quaternization reaction step which require the use of carcinogenic alkylating agents such as β-lactones and propane sultones. The prior art amphoteric surfactants require such quaternization step. The compounds of this invention are particularly useful in the preparation of aqueous fire fighting formulations, especially when used in combination with non-fluorinated surfactants. Such formulations have superior hydrocarbon fire fighting properties.

Preferred surfactants of this invention are the amphoteric surfactants of formulae Ia and IIa where Q is of structures (1a), (2a) or (3a). More preferred are those where $R_f$ is linear perfluoroalkyl of 6 to 12 carbon atoms, $R^1$ is ethylene and y is zero. The most preferred surfactants are those where X is NR and Q is of structure (1a) where $R^2$ is a straight chain alkylene of 2 to 5 carbon atoms, R is hydrogen, methyl or ethyl and $R^3$ and $R^4$ are methyl or ethyl.

The examples below are presented for illustrative purposes only and do not limit the scope of the invention. In the examples the surface tension was measured with a DuNouy tensiometer at 0.1% concentration in water at 25° C.

EXAMPLE 1

N-[3-(dimethylamino)propyl]-2 and 3-(1,1,2,2-tetrahydroperfluorodecylthio)succinamic acid

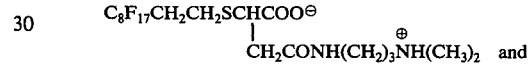

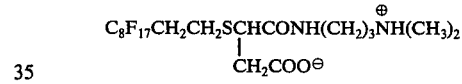

Maleic anhydride (10.0 g; 0.102 mole) and a mixture of ethylene glycol dimethyl ether (100 g) and N,N-dimethyl formamide (60 g) were placed in a stirred reaction flask kept under nitrogen atomsphere and cooled to 10° C in an ice bath. 3-dimethylaminopropylamine (10.4 g; 0.102 mole) was added drop-wise during one-half hour at a reaction temperature of 10°–15° C. The resulting white suspension was stirred at room temperature for 1 hour.

A small amount of this product was dried, washed with heptane and dried in vacuo at 30° C for 12 hours. Infrared analysis and NMR signals were characteristic for a compound of structure:

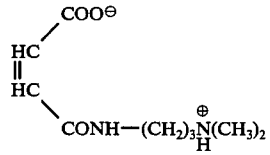

N-(3-dimethylaminopropyl) maleic acid amide. 1,1,2,2-tetrahydroperfluorodecyl mercaptan (49.0 g; 0.102 mole) was added all at once. The resulting mixture was stirred for 64 hours at room temperature. The thick suspension was filtered and the solids washed with acetone then dried at room temperature under vacuum (0.1 mm Hg) for 18 hours. The product was obtained as a white powder weighing 61.2 gms (yield = 88.2%) having a m.p. of 123°–128° with slow decomposition (gas evolution) above the melt. The infrared spectrum was consistent with the structure in particular the amide band at 1650 cm$^{-1}$ in the solid phase and at 1660 cm$^{-1}$ in dilute chloroform solution and the carboxylate asymmetrical and symmetrical stretching bands at 1550 cm$^{-1}$ and 1320 to 1390 cm$^{-1}$ respectively. An NMR spectrum was consistent with the structure and showed the following signals:

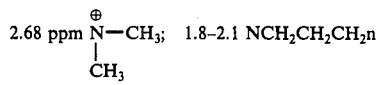

The surface tension ($\gamma$s) of the aqueous solution of the above named compound is 19.8 dynes/cm.

EXAMPLE 2

N-[3-(dimethylamino)propyl]-2 and 3-(1,1,2,2-tetrahydroperfluoroalkylthio)succinamic acid

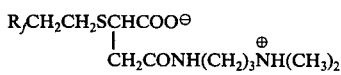

and its isomer.

Maleic anhydride (100 g; 1.02 mole) and N-methylpyrolidone (400 g) were stirred in a reaction flask under an inert atmosphere and cooled to 0° C in an ice-salt mixture. 3-Dimethylaminopropylamine (106 g; 1.04 mole) dissolved in N-methylpyrolidone (100 g) was added drop-wise during 40 minutes at 0°–10° C. The dark tan suspension was stirred at room temperature for 20 minutes when methanol (800 g) was added and the resulting mobile suspension was heated to 45° C. 1,1,2,2-Tetrahydroperfluoroalkyl mercaptan (483 g; 0.94 mole) (a mixture of compounds having varying alkyl groups as follows: $C_6$-25%; $C_8$-50%; and $C_{10}$-25%) was added during 10 minutes at 45°–50° C to give an amber solution which was stirred at 45° C for 3 hours. The completeness of reaction was checked by the disappearance of perfluoroalkylethyl mercaptan to trace amounts of the reaction mixture, as detected by gas chromatography. Identity of the product was confirmed by infrared absorption for the amide function at 1655 cm$^{-1}$ and the carboxylate ran at 1560 cm$^{-1}$ and 1325–1400 cm$^{-1}$. Gas chromatography showed three perfluoroalkyl acid areas, two solvent areas and trace areas due to the mercaptans. Proton NMR signals obtained were essentially identical to those for Example 1. The compound melted at 95° to 115° C. The surface tension of the aqueous solution of said compound was 17.7 dynes/cm.

Following the procedure described above, compounds analogous to Example 2 were prepared from maleic anhydride and the indicated starting materials:

| Ex. No. | R$_f$-thiol | Cationic Compound | $\gamma$ s (dynes/cm.) |
|---|---|---|---|
| 3 | $C_8F_{17}C_2H_4SH$ | $H_2N-N(CH_3)_2$ | 20.6 |
| 4 | $C_8F_{17}C_2H_4SH$ | $H_2N-CH_2CH_2-N(C_2H_5)_2$ | 17.3 |
| 5 | $C_8F_{17}C_2H_4SH$ | $HN(CH_3)-CH_2CH_2CH_2-N(CH_3)_2$ | 20.4 |
| 6 | $C_8F_{17}C_2H_4SH$ | $H_2N-CH_2CH_2CH_2-N(CH_2CH_2)_2O$ (morpholino) | 19.4 |
| 7 | $C_8F_{17}C_2H_4SH$ | $H_2N-CH_2CH_2-N(CH_3)_2$ | 17.9 |

EXAMPLE 8

N-methyl-N-(2'-N',N'-dimethylaminoethyl)-2 and 3-(1,1,2,2-tetrahydroperfluoroalkylthio)succinamic acid

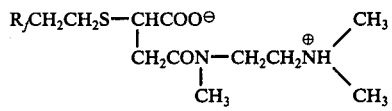

and isomer.

R$_f$ is a mixture of $C_6F_{13}$ (25%), $C_8F_{17}$ (50%) and $C_{10}F_{21}$ (25%).

Powdered maleic anhydride (0.033 moles, 3.24 g) was added in portions to a cooled solution of (N,N',N'-trimethyl)-ethylene-1,2-diamine (0.033 moles, 3.47 g) in 6.7 g water. The reaction was carried out under nitrogen and maintained at 10°–20° C with an ice bath. After the addition was complete the bath was removed and the reaction mixture was stirred at room temperature for 12 hours.

A small amount of the solution was dried in vacuo at 30° C for 12 hours. A dry, white powder was obtained whose NMR signals were characteristic for a compound of structure:

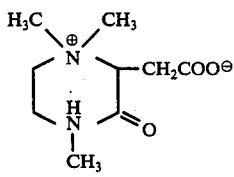

No acidic hydrogen could be titrated. 2-methyl-2,4-pentane diol (20.13 g) was added to the light yellow solution followed by perfluoroalkyl ethyl mercaptan (0.3135 moles, 14.65 g). The resulting white suspension was heated to 90° C with stirring until the completion of the reaction (6.5 hours). The clear light yellow solution was cooled to room temperature and diluted to 30% solids with water (23 g). The turbid solution was clarified by filtration (5μ porosity asbestos pad) to yield 66.5 g (93.4%) of a clear light yellow solution. Infrared analysis was consistent with the structure. The surface tension ($\gamma s$) of the aqueous solution of the above compound was 18.3 dynes/cm.

EXAMPLE 9

Following the above procedure, the compound N-ethyl-N-(2'-N'-dimethylaminoethyl)-2 and 3-(1,1,2,2-tetrahydroperfluoroalkylthio)succiniamic acid was prepared from maleic anhydride, $R_fC_2H_4SH$ and N,N-dimethyl-N'-ethyl-ethylene-1,2-diamine. The surface tension of this compound was 20.2 dynes/cm.

EXAMPLE 10

N-(2-dimethylaminoethyl)-2 and 3-(1,1,2,2-tetrahydroperfluoroalkylthio)succinamic acid

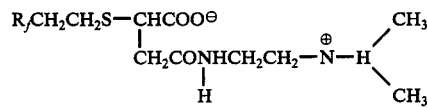

and isomer.

Powdered maleic anhydride (0.033 moles, 3.24 g) was added in portions to a cooled solution of (N,N-dimethyl)-ethane-1,2-diamine (0.033 moles, 2.90 g) in 6.7 g water. The reaction was carried out under nitrogen and maintained at 10°–20° C with an ice bath. After the addition was complete the bath was removed and the reaction mixture was stirred at room temperature overnight, 2-methyl-2,4-pentane diol (20.13 g) was added to the light yellow solution followed by perfluoroalkyl ethyl mercaptan (0.3135 moles, 14.65 g). The resulting white suspension was heated with stirring at 30° C to completion (6.5 hours). The light yellow solution was cooled to room temperature and diluted to 30% solids with water. It was clarified by filtration through a 5 m porosity asbestos pad to yield 66.5 g (93.4%) of a clear light yellow solution. The surface tension of the aqueous solution of the above compound was 22.0 dynes/cm.

Following the procedure described above, compounds analogous to Example 10 were prepared from maleic anhydride and the starting materials as shown below:

| Example No. | $R_f$-thiol | Cationic Compound | $\gamma s$ dynes/cm |
|---|---|---|---|
| 11 | $R_fC_2H_4SH$ | HN(C₂H₅)—CH₂CH₂—N(C₂H₅)₂ | 21.3 |
| 12 | $R_fC_2H_4SH$ | HN(C₂H₅)—CH₂CH₂CH₂—N(CH₃)₂ | 21.5 |
| 13 | $R_fC_2H_4SH$ | H₂N—CH₂CH₂CH₂—N(C₂H₅)₂ | 18.8 |
| 14 | $R_fC_2H_4SH$ | HN(CH₃)—CH₂CH₂CH₂—N(C₂H₅)₂ | 21.2 |
| 15 | $C_8F_{17}C_2H_4SH$ | 2-aminopyrimidine | 17.9 |
| 16 | $C_8F_{17}C_2H_4SH$ | 4-(aminomethyl)pyridine | 21.4 |
| 17 | $C_8F_{17}C_2H_4SH$ | N-methylpiperazine | 22.4 |
| 18 | $C_8F_{17}C_2H_4SH$ | 2-aminopyridine | 16.0 |

-continued

| Example No. | $R_f$-thiol | Cationic Compound | $\gamma$s dynes/cm |
|---|---|---|---|
| 19 | $C_8F_{17}C_2H_4SH$ | 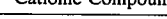 | 27.4 |
| 20 | $C_6F_{13}C_2H_4SH$ | $CH_3NHCH_2CH_2CH_2NH_2$ | 18.3 |
| 21 | $C_6F_{13}C_2H_4SH$ | $H_2NCH_2CH_2CH_2NH_2$ | 17.2 |

EXAMPLE 22

2 and 3-(1,1,2,2-tetrahydroperfluorodecylthio)succinic acid-mono-[2-(N,N-dimethyl)aminoethyl]ester

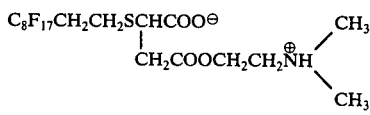

and isomer.

A solution of maleic anhydride (0.0408 moles, 4.00 g) in acetone (15 g) was added to N,N-dimethyl aminoethanol (0.0408 moles, 3.64 g) in acetone (10 g) at 10° C. The product precipitated as an acetone insoluble resin. After 30 minutes methanol (20 g) was added and a dispersion was formed. 1,1,2,2-tetrahydroperfluorodecyl mercaptan (.0408 moles, 19.6 g) was added and as the reaction proceeded, a clear solution was formed. The reaction was allowed to stand at room temperature for 24 hours. VPC and TLC showed no unreacted mercaptan. The yellow solution was dried under vacuum to a light yellow wax. The yield was 26.5 g (98.5%).

The surface tension ($\gamma$s) of the aqueous solution of the above named compound is 16.3 dynes/cm.

Following the procedure described above, compounds analogous to Example 22 were prepared from maleic anhydride and the starting materials shown below:

EXAMPLE 29

2 and 3-(1,1,2,2-tetrahydroperfluorodecylthio)succinic acid mono-(2'-quinolino ethyl) ester

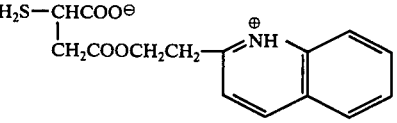

and isomer.

A solution of maleic anhydride (0.0255 moles, 2.5 g) in dichloromethane (10 g) was added dropwise to a stirred solution of 2-(2-hydroxyethyl)-quinoline (0.0255 moles, 4.2 g) in dichloromethane (20 g). The mixture was cooled to 0° C and kept at −10° C during the addition. After the addition was completed the dry ice/acetone bath was removed and the reaction mixture was allowed to warm up slowly to 20° C. Then 1,1,2,2-tetrahydroperfluorodecyl mercaptan (0.0255 moles, 12.24 g) were added. The brown solution was allowed to stand overnight at room temperature and then heated to 26° C for 2 hours. TLC and VPC showed no unreacted mercaptan. The solution was dried under vacuum to yield 18.2 g of a light brown powder (94.8%).

The surface tension ($\gamma$s) of the aqueous solution of the above named compound is 22 dynes/cm.

| Example No. | $R_f$-thiol | Cationic Compound | s dynes/cm |
|---|---|---|---|
| 23 | $C_8F_{17}C_2H_4SH$ | $CH_3-N(CH_2CH_2OH)_2$ | 19.0 |
| 24 | $C_8F_{17}C_2H_4SH$ | $HO-CH(CH_3)-CH_2N(C_2H_5)_2$ | 17.8 |
| 25 | $C_8F_{17}C_2H_4SH$ |  HO—CH$_2$CH$_2$—N(C$_5$H$_{10}$) | 17.4 |
| 26 | $C_8F_{17}C_2H_4SH$ |  HO—CH$_2$CH$_2$—N(C$_4$H$_8$)H | 17.4 |
| 27 | $C_8F_{17}C_2H_4SH$ | $H(OCH_2CH_2)_y-N(C_{18}H_{37})-(CH_2CH_2O)_xH$     x + y = 15 | 26.3 |
| 28 | $C_6F_{13}C_2H_4SH$ |  HO—CH$_2$CH$_2$—N(CH$_2$CH$_2$—OH)—CH$_2$—P(O)(OC$_2$H$_5$)$_2$ | 21.2 |

EXAMPLE 30

N,N'-bis[(n-propyl-3)-2 and 3-(1,1,2,2-tetrahydroperfluorooctylthio)succinamic monoamido]piperazine

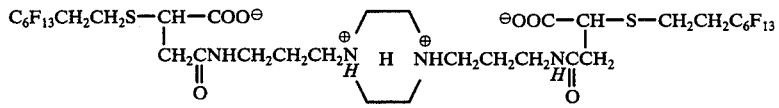

and isomer.

1,4-bis(3-aminopropyl)piperazine (0.0255 moles, 5.1 g) in 10 g acetone was added dropwise to a dry ice/isopropanol cooled solution of maleic anhydride (0.0510 moles, 5.0 g) at −10° to 0° C. A white precipitate came out immediately and the reaction mixture was stirred for 1 hour at 20° C.

1,1,2,2-tetrahydroperfluorooctyl mercaptan (0.0510 moles, 19.27 g) was added and the reaction was stirred for 3 days at room temperature until TLC showed no traces of unreacted mercaptan. The amber solution was dried under high vacuum to 29.1 g of yellow powder (99% yield).

Infrared spectrum was consistent for the structure.

The surface tension (γs) of the aqueous solution of the above named compound is 22 dynes/cm.

EXAMPLE 31

N-[3-(dimethylamino)propyl]-2 and 3-(heptafluoroisopropoxy-1,1,2,2-tetrahydroperfluoroalkylthio)succinamic acid

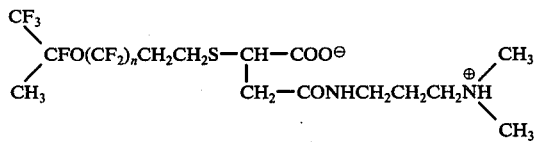

and isomer.

Maleic anhydride (0.0255 moles, 2.5 g) was dissolved in 10 g acetone. 3-dimethylamino propylamine (0.0255 moles, 2.61 g) in 5 g acetone was added dropwise so that the reaction temperature was maintained at 5°–10° C. As the reaction proceeded, an acetone insoluble resin was formed and after the amine addition was completed 10 g methanol was added to form a homogeneous mixture.

Heptafluoroisopropoxy-1,1,2,2-tetrahydroperfluoroalkyl mercaptan (0.0255 moles, 14.60 g) was added and the reaction mixture was stirred for 2 days until TLC showed no traces of the mercaptan. The pale yellow solution was dried under vacuum to give 18.9 g of white powder (95.9% yield).

Infrared analysis was consistent for the above structure.

EXAMPLE 32

N-[3-(dimethylamino)propyl]-2 and 3-(1,1,2,2-tetrahydroperfluorooctylthio)methylsuccinamic acid

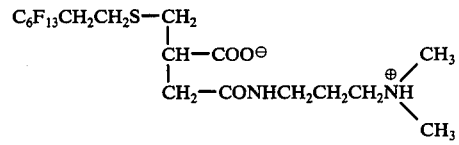

and isomer.

3-dimethylamino-propylamine (0.25 moles, 2.55 g) in 5 g acetone was added to a cooled solution of itaconic anhdyride (.025 moles, 2.80 g) in 10 g acetone at 5°–10° C. There was an immediate exothermic reaction and the light brown product precipitated out slowly. 10 g methanol was added to dissolve the product and the reaction mixture was stirred for 1 hour.

1,1,2,2-tetrahydroperfluorooctyl mercaptan (.025 moles, 9.45 g) was added and the reaction was stirred for 2 days at room temperature. TLC showed no unreacted mercaptan. The clear amber solution was dried under vacuum to give 14.0 g of a yellow wax (94.6% yield).

Infrared analysis was consistent with the above structure.

EXAMPLE 33

This example shows the preparation of sulfonates by quaternization with propane sultone.

41.7 g (0.061 moles) of the surfactant prepared in Example 1, was dissolved in an equal amount of acetone and 7.45 g (0.061 moles) of propane sultone was added; the reaction mixture was stirred at 50° C for 8 hours; the IR spectrum showed a strong new band at 1035 cm$^{-1}$ indicating, formation of the sulfonate; a C=O band at 1660 cm$^{-1}$ as well as bands at 1780 and 1710 cm$^{-1}$, indicating that some imide had been formed. No carboxylate and no dimethylamino group was visible in the IR spectrum which is generally consistent with the structure shown below. The product was a waxy solid which formed a strongly foaming aqueous solution.

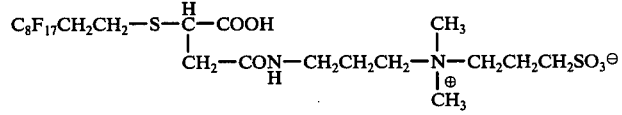

and its isomer.

| Elemental analysis: | C | N | S | F |
|---|---|---|---|---|
| Calculated: | 33.6 | 3.4 | 7.6 | 39.6 |
| Found: | 33.1 | 3.5 | 8.0 | 38.7 |

The surface tension (γs) of the aqueous solution of the above named compound is 21.5 dynes/cm.

On heating to 120° C for 30 minutes, its IR spectrum changed. The band at 1660 cm⁻¹ disappeared completely and the two imide bands at 1780 and 1720 cm⁻¹ grew very strong; no carboxylate and no dimethylamino absorption were present. This IR spectrum was consistent with the structure:

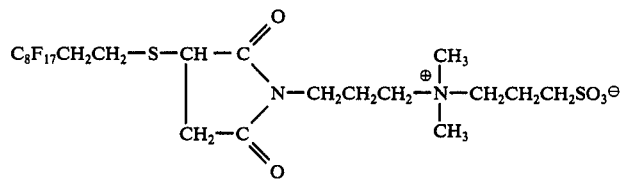

The surface tension (γs) of the aqueous solution of the above named compound is 22.5 dynes/cm.

EXAMPLE 34

Example 33 was repeated with the R$_f$-substituted succinamic acid of Example 16. The sulfonate (A) formed easily and was a waxy, brown solid. On heating imidization occurred to the compound of structure (B)

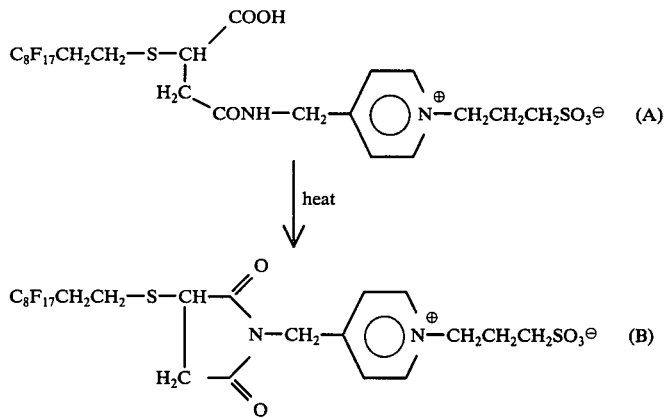

The surface tension (γs) of the aqueous solution of the above named compound is 19.1 dynes/cm.

IR analysis of (A) and (B) were consistent with the given structures.

Elemental analysis of (B)

|  | C | N | S | F |
|---|---|---|---|---|
| Calculated: | 33.4 | 3.4 | 7.7 | 38.8 |
| Found: | 34.6 | 3.3 | 8.1 | 37.2 |

EXAMPLE 35

This example shows the formation of R$_f$-substituted succinimide from the corresponding succinamic acid.

IR analysis of the compound made in Example 1 revealed a strong carboxylate band at 1600 cm⁻¹ and a strong C=O band at 1660 cm⁻¹ consistent with structures:

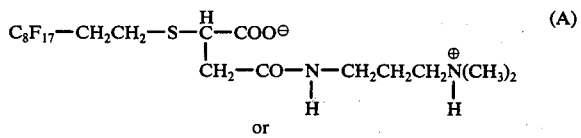

or $$C_8F_{17}-CH_2CH_2-S-\overset{H}{\underset{|}{C}}-CON-CH_2CH_2CH_2\overset{\oplus}{N}(CH_3)_2 \quad (A')$$
$$\underset{CH_2-COO^\ominus}{|} \quad \underset{H}{|}$$

When this material was heated to 120° C for 20 minutes, it foamed slightly; it became insoluble in water, but dissolved in acidic aqueous medium. Its IR analysis showed two strong bands at 1780 and 1710 cm⁻¹ characteristic for the cyclic imide with the bands at 1600 and 1660 cm⁻¹ reduced to weak shoulders; also present was a strong absorption at 2770 and 2820 cm⁻¹ characteristic for the dimethyl amino group. The spectrum was consistent with the structure:

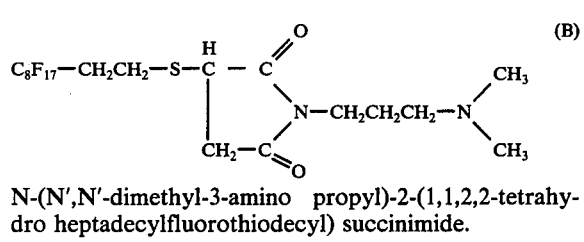

N-(N',N'-dimethyl-3-amino propyl)-2-(1,1,2,2-tetrahydro heptadecylfluorothiodecyl) succinimide.

| Elemental Analysis for (B): | | | | |
|---|---|---|---|---|
|  | C | N | S | F |
| Calculated: | 33.4 | 4.1 | 4.7 | 47.5 |
| Found: | 34.2 | 4.0 | 5.3 | 46.4 |

The following examples describe the preparation of additional quaternized derivatives.

EXAMPLE 36

2.04 g (0.003 mole) of [2 and 3-(1,1,2,2-tetrahydroperfluorodecyl thio)]-N,N-dimethyl(3-aminopropyl) succiniamic acid (of Example 1) were dissolved in 5cc 35% aqueous HCl. The clear solution was evaporated and the residue dried in vacuo (0.1 mm Hg) at 80° C for 12 hours, to yield 2.1 g of a white powder, having the structure:

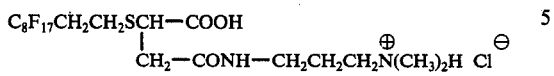

and isomer.

The surface tension (γs) of the aqueous solution of the above named compound is 18.8 dynes/cm.

EXAMPLE 37

2.04 g (0.003 mole) of 2 and 3-(1,1,2,2-tetrahydroperfluorodecylthio)-N,N-dimethyl aminopropyl succinamic acid melting at 123°–218° C was sealed in an ampoule with 0.43 g (0.003 mole) methyl iodide in 10 g isopropanol and heated for 3 hours. The pale pink suspension was filtered and dried to yield 1.6 g of white powder melting at 205°–250° C having the structure

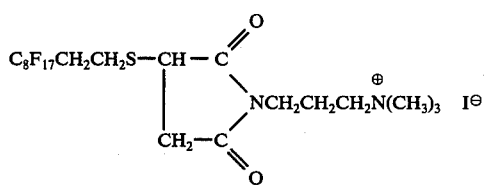

The surface tension (γs) of the aqueous solution of the above named compound is 24.9 dynes/cm.

EXAMPLE 38

2.04 g (0.003 mole) of 2 and 3-(1,1,2,2-tetrahydroperfluorodecylthio)-N,N-dimethyl(3-aminopropyl) succiniamic acid was refluxed with 0.38 g (0.003 mole) benzyl chloride in 10 g ethanol until basic tertiary amine was no longer detected. The solution was evaporated to yield 2.17 g of an off-white semi-solid having the structure

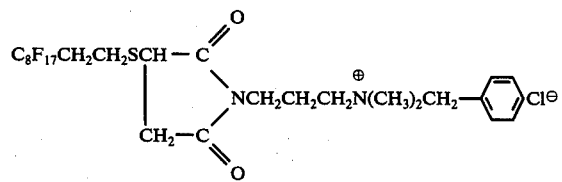

The surface tension (γs) of the aqueous solution of the above named compound is 20.8 dynes/cm.

EXAMPLE 39

2.04 g (0.003 mole) of [2 and 3-(1,1,2,2-tetrahydroperfluorodecylthio)]-N,N-dimethyl(3-aminopropyl)succinamic acid was stirred with 0.28 g (0.003 mole) chloroacetic acid in 30 g water overnight. No free tertiary amine was detectable. 20 g methanol was added to break the foam and the clear solution was evaporated at 60° C and vacuum to give 2.1 g of off-white wax having the structure

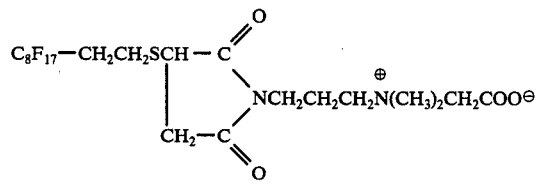

The surface tension (γs) of the aqueous solution of the above named compound is 17.4 dynes/cm.

EXAMPLE 40

2.04 g (0.003 mole) of [2 and 3-1,1,2,2-tetrahydroperfluorodecylthio]-N,N-dimethyl(3-amino propyl)succiniamic acid was dissolved in 30 ml ether. A solution of 0.22 g (0.0031 mole) β-propiolactone in 5 ml ether was added dropwise over 5 minutes at 15° C. The mixture was stirred for 2 hours at 30° C and the ether was removed in a rotary evaporator. Yield: 2.2 g of a product having the structure:

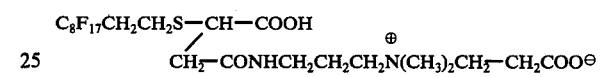

and isomer.

The surface tension (γs) of the aqueous solution of the above named compound is 22.6 dynes/cm.

What is claimed is:

1. A compound of the formula

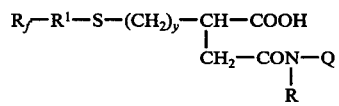

or its amphoteric tautomer or of the formula

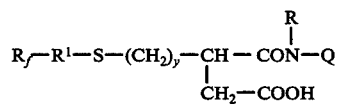

or its amphoteric tautomer or a mixture thereof wherein
$R_f$ is straight or branched chain perfluoroalkyl of 1 to 18 carbon atoms or said perfluoroalkyl substituted by perfluoroalkoxy of 2 to 6 carbon atoms;
$R^1$ is branched or straight chain alkylene of 1 to 12 carbon atoms;
$Y$ is 1 or zero;
$R$ is hydrogen, alkyl of 1 to 6 carbon atoms or hydroxyalkyl of 1 to 6 carbon atoms, and
$Q$ is an aliphatic amino group of the formula

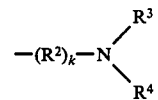

wherein
$R^2$ is a linear or branched alkylene of 2 to 12 carbon atoms;
$k$ is 1 or zero;
$R^3$ and $R^4$ are independently of each other hydrogen, alkyl of 1 to 20 carbon atoms or said alkyl substituted by an alkyl group of 1 to 5 carbons.

2. A compound of claim 1 represented by formula I or II wherein
R¹ is alkylene
Q is an aliphatic amino group of the formula

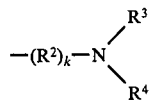

where R³ and R⁴ are hydrogen or alkyl.

3. A compound of claim 1 wherein
R² is straight or branched chain alkylene of 2 to 5 carbon atoms,
Y is zero,
R³ and R⁴ are each alkyl group of 1 to 5 carbons.

4. A compound of claim 3 wherein
R¹ is ethylene and
R³ and R⁴ are methyl or ethyl.

5. A compound of claim 4 of formula I or II wherein $R_f$ is $C_8F_{17}$—, R is H—, R² is —$CH_2$—, $k$ is one and R³ and R⁴ are each $CH_3$—, or a mixture thereof.

6. A compound of claim 4 of formula I or II wherein about 25% of $R_f$ are perfluoroalkyl groups of 6 carbon atoms, about 50% of $R_f$ are perfluoroalkyl groups of 8 carbon atoms and about 25% of $R_f$ are perfluoroalkyl groups of 10 carbon atoms, R is H—, R² is —$CH_2$—, $k$ is one and R³ and R⁴ are each $CH_3$—, or a mixture thereof.

7. A compound of claim 4 of formula I or II wherein $R_f$ is $C_8F_{17}$—, R is H—, $k$ is zero, and R³ and R⁴ are each $CH_3$—, or a mixture thereof.

8. A compound of claim 4 of formula I or II wherein $R_f$ is $C_8F_{17}$—, R is H—, R² is —$CH_2$—, $k$ is one and R³ and R⁴ are each $C_2H_5$—, or a mixture thereof.

9. A compound of claim 4 of formula I or II wherein $R_f$ is $C_8F_{17}$—, R is $CH_3$—, R² is —$CH_2$—, $k$ in one and R³ and R⁴ are each $CH_3$—, or a mixture thereof.

10. A compound of claim 4 of formula I or II wherein $R_f$ is $C_8F_{17}$—, R is H—, R² is —$CH_2$—, $k$ is one and R³ and R⁴ are each $CH_3$—, or a mixture thereof.

11. A compound of claim 4 of formula I or II wherein about 25% of $R_f$ are perfluoroalkyl groups of 6 carbon atoms, 50% of $R_f$ are perfluoroalkyl groups of 8 carbon atoms and about 25% of $R_f$ are perfluoroalkyl groups of 10 carbon atoms, R is $CH_3$—, R² is —$CH_2CH_2$—, $k$ is one and R³ and R⁴ are each $CH_3$—, or a mixture thereof.

12. A compound of claim 4 of formula I or II wherein about 25% of $R_f$ are perfluoroalkyl groups of 6 carbon atoms, 50% of $R_f$ are perfluoroalkyl groups of 8 carbon atoms and about 25% of $R_f$ are perfluoroalkyl groups of 10 carbon atoms, R is $C_2H_5$—, R² is —$CH_2CH_2$—, $k$ is one and R³ and R⁴ are each $CH_3$—, or a mixture thereof.

13. A compound of claim 1 wherein R' is ethylene, $y$ is zero, R is hydrogen, R² is ethylene, $k$ is one and R³ and R⁴ are each methyl, or a mixture of isomers.

* * * * *